United States Patent [19]

Blank et al.

[11] Patent Number: 4,760,209
[45] Date of Patent: Jul. 26, 1988

[54] PROCESS FOR PREPARING 3,5-DICHLORO-α-METHYLSTYRENE

[75] Inventors: Heinz U. Blank, Odenthal; Erich Wolters, Cologne; Bernhard Beitzke, Bergisch-Gladbach; Karlfried Wedemeyer, Cologne; Michael Herzhoff, Much; Karl-Wilhelm Henneke, Leverkusen; Guido Steffan, Odenthal; Otto Neuner, Bergisch-Gladbach, all of Fed. Rep. of Germany

[73] Assignee: Bayer Aktiengesellschaft, Leverkusen, Fed. Rep. of Germany

[21] Appl. No.: 940,691

[22] Filed: Dec. 11, 1986

Related U.S. Application Data

[63] Continuation of Ser. No. 764,892, Aug. 12, 1985, abandoned.

[30] Foreign Application Priority Data

Aug. 29, 1984 [DE] Fed. Rep. of Germany ....... 3431697

[51] Int. Cl.$^4$ .................... C07C 17/34; C07C 17/00; C07C 17/24
[52] U.S. Cl. .................................... 570/200; 570/202
[58] Field of Search ............................... 570/200, 202

[56] References Cited

U.S. PATENT DOCUMENTS

| | | | |
|---|---|---|---|
| 2,920,109 | 1/1960 | Angelkorte | 570/202 |
| 3,553,274 | 1/1971 | Lewis et al. | 570/143 |
| 4,059,642 | 11/1977 | Dewald et al. | 570/190 |
| 4,087,473 | 5/1978 | Markley | 570/197 |
| 4,347,390 | 8/1982 | Nishiyama et al. | 570/202 |
| 4,348,265 | 9/1982 | Strom | 570/197 |
| 4,686,311 | 8/1987 | Jackisch | 570/200 |

FOREIGN PATENT DOCUMENTS

2907666 9/1979 Fed. Rep. of Germany ...... 570/200

OTHER PUBLICATIONS

Bachman et al, J. Am. Chem. Soc., 70 (1948) pp. 1772–1774.
Cubbon et al, The Properties of Nuclear Brominated Styrenes I, pp. 479–483.

Primary Examiner—J. E. Evans
Attorney, Agent, or Firm—Sprung, Horn, Kramer & Woods

[57] ABSTRACT

In the preparation of 3,5-dichloro-α-methylstyrene by isopropylation of an m/p-dichlorobenzene mixture, isomerization of the resulting alkylation mixture, subsequent side chain bromination of the alkylation mixture and dehydrobromination of the resulting bromination mixture, the improvement which comprises reacting an excess of an m/p-dichlorobenzene mixture which contains at least 50% by weight of m-dichlorobenzene with isopropyl halide, isomerizing the resulting alkylation mixture under pressure in the presence of aluminum chloride until thermodynamic equilibrium has been attained, separating off the isomerized alkylation mixture from the unreacted m/p-dichlorobenzene mixture, and recycling the unreacted mixture for further reaction.

17 Claims, No Drawings

PROCESS FOR PREPARING 3,5-DICHLORO-α-METHYLSTYRENE

This is a continuation, of application Ser. No. 764,892, filed Aug. 12, 1985, now abandoned.

The invention relates to a process for preparing 3,5-dichloro-α-methylstyrene by isopropylation of an m/p-dichlorobenzene mixture, isomerization of the resulting alkylation mixture, subsequent side chain bromination of the alkylation mixture and dehydrobromination of the resulting bromination mixture.

U.S. Pat. No. 3,553,274 discloses a process for preparing 3,5-dichlorocumene by reacting m-dichlorobenzene with isopropyl bromide in the presence of aluminum chloride (cf., for example, Example 1 of said U.S. Patent). The reaction is carried out therein with pure m-dichlorobenzene in a ratio of 1:1 with isopropyl bromide in the presence of 20 mol % of aluminum chloride, relative to the alkylating agent, 2,4-dichlorocumene being obtained first. The hydrogen bromide liberated in the course of the alkylation is condensed by means of a dry ice cooler and as a result can react with the aluminum chloride to form the following possible complexes: HAlBrCl$_3$, HAlBr$_2$Cl$_2$, HAlBr$_3$Cl or HAlBr$_4$.

As only one such complex formed from aluminum chloride and hydrogen bromide is described and claimed as a catalyst suitable for isomerizing the 2,4-dichlorocumene formed in the alkylation step to 3,5-dichlorocumene, alkylation and isomerization are advantageously carried out as a single-vessel reaction, thereby utilizing the hydrogen bromide liberated in the course of the alkylation. According to our calculations, the resulting yield is only 62.5%, and the product after aqueous working up is an isomeric mixture which consists of 20% of 2,4-dichlorocumene and 80% of 3,5-dichlorocumene. The disadvantages with the process described in said U.S. Pat. No. 3,553,274 are on the one hand the high cost of pure m-dichlorobenzene and of the alkylating agent isopropyl bromide and on the other the relatively low yield of 2,4- and 3,5-dichlorocumene mixture.

U.S. Pat. No. 4,059,642 discloses the selective alkylation of m-dichlorobenzene out of an m/p-dichlorobenzene mixture by means of sufficiently small amounts of aluminum chloride. According to Example 1 of said patent, a dichlorobenzene mixture containing 62.3% of m-dichlorobenzene and 37.7% of p-dichlorobenzene is alkylated at 20° C. in a molar ratio of 3.5:1 with isopropyl chloride in the presence of 0.69 mol % of aluminum chloride, relative to starting m/p-dichlorobenzene mixture. Aqueous working up gave 221 g of organic phase, which was subsequently subjected to fractional distillation, which produced 46 g of a fraction which, according to analysis by gas chromatography, consisted of 99.7% of 2,4-dichlorocumene. The 2,5-dichlorocumene content, formed by alkylation of the p-dichlorobenzene which is present, was said to be less than 1%. This low 2,5-dichlorocumene level shows that, in the alkylation of m-dichlorobenzene mixtures, it is possible to obtain selective alkylation of the m-dichlorobenzene content out of the mixture if the aluminum chloride concentration, as claimed, is very low and the reaction temperatures are below 60° C.

The excess, unreacted m/p-dichlorobenzene mixture recovered from the distillation has a different composition than the starting mixture in the alkylation. Thus, the dichlorobenzene mixture used in excess for the alkylation contains 62.3% of m-dichlorobenzene and 37.7% of p-dichlorobenzene; the mixture recovered after selective alkylation of the m-dichlorobenzene consists of 54.7% of m-dichlorobenzene and 45.3% of p-dichlorobenzene. The selective alkylation of m-dichlorobenzene out of an m/p-dichlorobenzene mixture leads through the removal of m-dichlorobenzene in the form of 2,4-dichlorocumene to an increase in the concentration of p-dichlorobenzene. If it is a precondition that the m/p-dichlorobenzene mixture used in the alkylation should always be of constant composition, it is necessary that the recovered m/p-dichlorobenzene mixture is concentrated either by costly distillation or by adding pure m-dichlorobenzene before being recycled to alkylation and isomerization. However, it is technically complicated to carry out a distillation or a concentrating step and it has an adverse effect on the economics of the process.

A process has now been found for preparing 3,5-dichloro-α-methylstyrene by isopropylation of an m/p-dichlorobenzene mixture, isomerization of the resulting alkylation mixture, subsequent side chain bromination of the alkylation mixture and dehydrobromination of the resulting bromination mixture, which is characterized in that an m/p-dichlorobenzene mixture which contains at least 50% by weight of m-dichlorobenzene is reacted in excess with isopropyl halide, the resulting alkylation mixture is isomerized under pressure in the presence of aluminum chloride until thermodynamic equilibrium has been attained and, after the isomerized alkylation mixture has been separated off, the unreacted m/p-dichlorobenzene mixture is returned to the reaction.

The m/p-dichlorobenzene mixture used in the process according to the invention contains at least 50% by weight of m-dichlorobenzene. Preferably the dichlorobenzene mixture used contains 65 to 99% by weight, particularly preferably 75 to 98% by weight, of m-dichlorobenzene and 1 to 35% by weight, in particular 2 to 25% by weight, of p-dichlorobenzene. Very particularly preferably the m/p-dichlorobenzene mixture used in the process according to the invention contains 85% by weight of m-dichlorobenzene and 15% by weight of p-dichlorobenzene.

In the process according to the invention, the m/p-dichlorobenzene mixture is reacted with isopropyl halide, such as isopropyl chloride and isopropyl bromide, preferably isopropyl chloride. In said reaction the m/p-dichlorobenzene mixture is preferably fed in in excess, relative to the isopropyl halide feed. The molar ratio of m/p-dichlorobenzene mixture to isopropyl halide feed is preferably 4:1 to 1.1:1, particularly preferably 2.5:1 to 1.1:1.

The amount of aluminum chloride feed is generally about 0.6 to 50, preferably 5 to 30, particularly preferably 18 to 25 mol %, relative to isopropyl halide feed.

The reaction is carried out within the temperature range from about −10° C. to +80° C., preferably +10° to +70° C., particularly preferably +20° to +60° C.

The alkylation mixture in the process according to the invention is isomerized under pressure until thermodynamic equilibrium has been attained. For example, the thermodynamic equilibrium on feeding in an m/p-dichlorobenzene mixture which contains 85% by weight of m-dichlorobenzene and 15% by weight of p-dichlorobenzene is at about 10% of 2,5-, about 20% of 2,4- and about 70% of 3,5-dichlorocumene. The pressure at said equilibrium is about 1 to 20 bar, preferably 1 to 15 bar, particularly preferably 1 to 10 bar. The attainment of thermodynamic equilibrium can be readily monitored by conventional analytical methods. The rate at which thermodynamic equilibrium is attained chiefly depends on the level of aluminum chloride feed, on the reaction temperature, and on the pressure.

The addition of catalytic amounts of a conventional phase transfer catalyst, such as tetraethylammonium chloride, or the addition of catalytic amounts of 1,2-propanediol can have a significant accelerating effect on the attainment of equilibrium between the isomers in the dichlorocumene mixture or permit a drastic reduction in the amount of aluminum chloride required. It has been found to be suitable to add customary phase transfer catalysts in amounts of about 0.1 to 10, preferably 1 to 4, mol %, relative to the isopropyl halide feed. The 1,2-propanediol can be added to the process according to the invention in amounts of about 1 to 10 mol %, preferably 2 to 5 mol %. It is possible to use the phase transfer catalyst and 1,2-propanediol in the process according to the invention both individually or mixed with each other.

The resulting reaction mixture is hydrolyzed in conventional manner, for example by stirring into ice-water. After the organic phase has been separated off the m/p-dichlorobenzene mixture used in excess and not fully reacted is removed by distillation. The m/p-dichlorobenzene mixture is generally removed by distillation in vacuo under about 1 to 30 mbar, preferably 10 to 20 mbar.

The m/p-dichlorobenzene mixture recovered in this way always has a constant composition which differs only insignificantly from that of the feed mixture, and can thus be directly returned to the reaction.

It is thus possible to circulate the recovered, excess m/p-dichlorobenzene mixture as often as is desired without any significant change in the composition of the mixture compared to the feed mixture.

The dichlorocumene mixture obtained after the excess m/p-dichlorobenzene mixture has been separated off and essentially comprising 2,4- and 3,5-dichlorocumene is subsequently subjected to a side chain bromination, and the resulting bromination mixture is subjected to dehydrobromination. In the bromination, the 3,5-dichlorocumene is selectively brominated to 3,5-dichloro-α-bromocumene. The other two isomers, namely 2,5- and 2,4-dichlorocumene, are left behind in substantially unbrominated form. The bromination can be carried out in the manner described in U.S. Pat. No. 4,087,473, namely at temperatures of about 15° to 65° C. using a brominating agent, such as elemental bromine, in the presence of a free-radical former, such as benzoyl peroxide.

The resulting bromination mixture is subsequently dehydrobrominated under alkaline conditions in conventional manner, for example with isobutylate (cf. Houben-Weyl V/1b, page 134 et seq., Georg Thieme Verlag Stuttgart, 1972) 2,5- and 2,4-dichlorocumene being separated by distillation from the 3,5-dichloro-α-methylstyrene formed from 3,5-dichloro-α-bromocumene.

In the process according to the invention, 3,5-dichloro-α-methylstyrene is obtained in high yields and in high purities.

The economics of the process according to the invention are particularly favorable owing to the use of technical m/p-dichlorobenzene mixtures. A particularly surprising aspect of the process is that the excess m/p-dichlorobenzene recovered from the alkylation and isomerization of the feed m/p-dichlorobenzene mixture always has the composition of the feed dichlorobenzene mixture and, therefore, need not be subjected to a technically complicated distillation or concentrating step before being returned to the reaction. This is because it seemed likely that for statistical reasons the m-dichlorobenzene in the mixture would be alkylated preferentially, resulting in an increase in the concentration of the p-dichlorobenzene in the mixture. A consequence would then have been that it would no longer have been possible simply to return the mixture without topping up the m-dichlorobenzene portion therein.

The following examples are intended to illustrate the process according to the invention without, however, restricting it thereto.

EXAMPLE 1

(a) Alkylation and isomerization

An enamelled 1.3 liter stirred autoclave was charged with 955.5 g (6.5 mols) of a mixture of 85% strength m-dichlorobenzene and 15% strength p-dichlorobenzene and with 216.1 g (1.63 mols) of AlCl$_3$. 255.1 g (3.25 mols) of isopropyl chloride were pumped in with stirring at room temperature in the course of 5 minutes, during which the internal temperature in the autoclave rose to 35° C. and the resulting HCl pressure was maintained at 5 bar by blowing off. After the addition by pumping had ended, the temperature was raised to 50° C. (in the course of about 7 minutes) during which the pressure was again maintained at 5 bar by blowing off. Stirring was continued for 10 hours at 50° C./5 bar of HCl pressure.

After the reaction had ended, the autoclave was allowed to cool down, the pressure was let off, and the contents were sucked out on to 2 liters of water, for hydrolysis. The mixture was stirred until it had become colorless, and was transferred into a separating funnel, and the organic phase was separated from the aqueous phase. This produced 1,026 g of organic material. The distillation was then carried out under a water jet vacuum in a 40 cm silver-jacketed column filled with 10 mm Raschig glass rings. 574.4 g of m/p-dichlorobenzene mixture (60% of the starting amount) having a composition of 85.4% of m- and 14.6% of p-dichlorobenzene were recovered. The 424.1 g of isomeric mixture obtained, comprising 9.7% of 2,5-, 20.6% of 2,4- and 69.56% of 3,5-dichlorocumene, corresponded to a 69% yield. The following table shows in condensed form the composition of the m/p-dichlorobenzene mixtures after alkylation and isomerization and before reuse after replenishment with fresh mixture.

(b) Bromination

A 4 liter four-necked flask mixing apparatus was charged with 848.2 g 4.5 mols) of isomeric mixture (9.7% of 2,5-, 20.6% of 2,4- and 69.56% of 3,5-dichlorocumene) and 1,200 ml of carbon tetrachloride, and the temperature was raised to 30° C. 508.6 g (3.18 mols) of bromine were metered at 30° to 40° C. underneath the surface of the reaction mixture in the course of 5 to 6 hours, while the mixture was exposed to radiation.

After the colorless mixture had been subsequently stirred for 5 minutes, carbon tetrachloride was distilled off in a rotary evaporator under an increasing vacuum at, in the end, a bottom temperature of 90°–100° C. and a pressure of 40 mbar.

The result was 1,131 g of crude bromination mixture.

(c) The elimination of hydrogen bromide with isobutylate 1,366 g of isobutanol were heated to the boil in the absence of moisture in a 4 liter four-necked flask stirring apparatus equipped with an internal thermometer, a stirrer, a dropping funnel and a 50 cm packed column (4×4 mm Raschig rings) on top, and 904 g of 30% strength sodium methylate solution (271.23 g, 100%; 5.02 mol) were added in the course of about 30 minutes. Solvent was taken off at the top until the bottom temperature was 139° C. 1,125 g of crude bromination mixture were added dropwise in the course of an hour, during which the bottom temperature dropped to 125° C. At the same time 454 g of isobutanol were taken off at the top. The mixture was afterwards stirred at 125° C. for 1 hour, was cooled down to room temperature, and 800 g of water were added to it, and excess base was subsequently neutralized with 179 g of 30% strength hydrochloric acid. The aqueous phase was separated off, and the organic phase was washed with 400 ml of 20% strength sodium chloride solution and then distilled over a 20 cm Vigreux column. The main fraction (757 g) distilled over at 100°–128° C. under 20 mbar and consisted of 68.5% of 3,5-dichloro-α-methylstyrene. Yield: 89% of theory.

The fractional precision distillation carried out subsequently yielded 3,5-dichloro-α-methylstyrene in 99% purity (boiling point: 111°–113° C./18–20 mbar).

EXAMPLE 2

In a batch carried out in fundamentally the same way as described in Example 1, a 1.3 liter autoclave was charged with 956 g (6.5 mols) of 85% strength m-dichlorobenzene (15% p-dichlorobenzene) and 87 g (0.65 mol) of AlCl$_3$, together with 11 g (0.065 mol) of tetraethylammonium chloride. 255 g (3.25 mols) of isopropyl chloride were pumped in. 10 hours of isomerization at 50° C. and 5 bar of HCl pressure, followed by aqueous working up and distillation, produced 430.96 g of isomeric mixture which consisted of 10.1% of 2,5-, 22.5% of 2,4- and 67.3% of 3,5-dichlorocumene. Their yield was 70.16%. 59.3% of the feed m/p-dichlorobenzene mixture was recovered by distillation, the composition being 86.3% of m- and 13.6% of p-dichlorobenzene. The further conversion to 3,5-dichloro-α-methylstyrene was carried out as in Example 1.

EXAMPLE 3

The same batch as in Example 2. Tetraethylammonium chloride was replaced by 15 g (0.065 mol) of triethylbenzylammonium chloride. 415.77 g of isomeric mixture consisting of 10.0% of 2,5-, 22.7% of 2,4- and 67.3% of 3,5-dichlorocumene were obtained, which corresponded to a yield of 67.7%. 59.3% of the m/p-dichlorobenzene feed was recovered by distillation (566.34 g), the composition being according to GC analysis 86.3% of m- and 13.7% of p-dichlorobenzene. The further conversion to 3,5-dichloro-α-methylstyrene was carried out as in Example 1.

EXAMPLE 4

The same batch as in Example 2. Tetraethylammonium chloride was replaced by 21.0 g (0.065 mol) of tetrabutylammonium bromide. 465.98 g of isomeric mixture consisting of 9.7% of 2,5-, 20.7% of 2,4- and 69.5% of 3,5-dichlorocumene were obtained, which corresponded to a yield of 75.8%. 55.4% of the m/p-dichlorobenzene mixture feed was recovered by distillation (529.11 g), the composition being according to GC analysis 85.65% of m- and 14.35% of p-dichlorobenzene. The further conversion to 3,5-dichloro-α-methylstyrene was carried out as in Example 1.

EXAMPLE 5

A 2 liter autoclave was charged with 1,470 g (10.0 mols of 85% strength m-dichlorobenzene (15% of p-dichlorobenzene) and 133 g (1.0 mol) of AlCl$_3$. 413 g (5.0 mols) of isopropyl chloride were pumped in at room temperature with stirring in the course of 35 minutes during which the resulting HCl pressure was maintained at 5 bar by continuously blowing off. 15.2 g (0.2 mol) of 1,2-propanediol were added to the final 150 ml of isopropyl chloride to be pumped in, and were pumped in together with the isopropyl chloride. After the addition by pumping was complete, the autoclave was raised to 50° C. while the pressure was again maintained at a constant 5 bar by blowing off. Stirring was continued for 10 hours at 50° C./5 bar of HCl pressure. After the reaction had ended, the autoclave was cooled down, the pressure was let off, and the contents were sucked out on to 2 liters of ice-water, for hydrolysis. Stirring was continued until the mixture had become colorless, and the organic phase was then separated from the aqueous phase in a separating funnel. The subsequent distillation in a 40 cm silver-jacketed column packed with 4 mm Raschig glass rings produced a dichlorocumene mixture which passed over at 102–103° C./18 bar and consisted of 10.8% of 2,5-, 21.6% of 2,4- and 67.5% of 3,5-dichlorocumene. The yield was 84.6% of theory. 53.25% of the feed m/p-dichlorobenzene mixture was recovered (782.8 g), having a composition of 84.86% of m- and 15.14% of p-dichlorobenzene. The further conversion to 3,5-dichloro-α-methylstyrene was carried out as in Example 1.

| Number of returns | m/p-dichlorobenzene mixture recovered out of the reaction | | | | | Addition of dichlorobenzene mixture (85% meta-dichlorobenzene) | | | resulting composition of the new feed mixture | | | |
|---|---|---|---|---|---|---|---|---|---|---|---|---|
| | Total amount [g] | m [g] | m [%] | p [g] | p [%] | Total amount [g] | m [g] | p [g] | m [g] | m [%] | p [g] | p [%] |
| 1 | 452 | 381.67 | 84.4 | 70.0 | 15.5 | 503.5 | 427.95 | 75.52 | 809.6 | 84.76 | 145.56 | 15.24 |
| 2 | 574.4 | 483.34 | 84.15 | 91.05 | 15.85 | 381.10 | 323.94 | 57.16 | 807.3 | 84.5 | 148.2 | 15.5 |
| 3 | 463 | 385.7 | 83.3 | 76.4 | 16.5 | 492.45 | 418.6 | 73.86 | 804.4 | 84.26 | 150.22 | 15.74 |
| 4 | 535 | 442.14 | 83.7 | 86.16 | 16.30 | 420.42 | 357.4 | 63.06 | 799.5 | 84.27 | 149.22 | 15.73 |
| 5 | 528 | 435.62 | 83.7 | 84.63 | 16.30 | 435.87 | 370.5 | 65.4 | 806.10 | 84.31 | 150.0 | 15.70 |
| 6 | 507 | 418.31 | 83.54 | 82.42 | 16.5 | 448.50 | 381.22 | 67.275 | 799.54 | 84.23 | 149.7 | 15.77 |
| 7 | 515 | 436.62 | 85.4 | 74.56 | 14.6 | 445.0 | 378.25 | 66.75 | 814.87 | 85.22 | 141.31 | 14.778 |
| 8 | 531 | 444.20 | 83.80 | 85.67 | 16.17 | 425.0 | 361.25 | 63.75 | 805.45 | 84.40 | 149.42 | 15.65 |

It will be understood that the specification and examples are illustrative but not limitative of the present invention and that other embodiments within the spirit and scope of the invention will suggest themselves to those skilled in the art.

We claim:

1. In the preparation of 3,5-dichloro-α-metylstyrene by isoporpylation of an m/p-dichlorobenzene mixture, isomerization of the resulting alkylation mixture, subsequent side chain bromination of the alkylation mixture and dehydrobromination of the resulting bromination mixture, the improvement which comprises reacting an m/p-dichlorobenzene feed mixture which contains 65 to 99% by weight of m-dichlorobenzene with isopropyl chloride, the molar ratio of the m/p-dichlorobenzene mixture to the isopropyl halide being 4:1 to 1.1:1, isomerizing the resulting alkylation mixture under a pressure of 1 to 20 bar and at a temperature of −10° to +80° C. in the presence of aluminum chloride, the aluminum chloride being employed in a 18 to 50 mole % relative to the isopropyl chloride, until thermodynamic equilibrium has been attained, separating off the isomerized alkylation mixture from the unreacted m/p-dichlorobenzene mixture, and recycling the unreacted mixture which differs only insignificantly from that of the m/p-dichlorobenzene feed mixture for further reaction.

2. A process according to claim 1, wherein the m/p-dichlorobenzene feed mixture contains 75 to 98% by weight of m-dichlorobenzene.

3. A process according to claim 1, wherein the molar ratio of m/p-dichlorobenzene feed mixture to isopropyl chloride is 2.5:1 to 1.1:1.

4. A process according to claim 1, wherein the aluminum chloride is used in 5 to 30 mol %, relative to isopropyl chloride.

5. A process according to claim 2, wherein the molar ratio of m/p-dichlorobenzene feed mixture to isopropyl halide is 2.5:1 to 1.1:1, the aluminum chloride is used in 5 to 30 mol %, relative to isopropyl chloride, and the isomerization temperature is −10° to +80° C.

6. A process according to claim 1, wherein the aluminum chloride is used in 18 to 25 mole %, relative to the isopropyl chloride.

7. A process according to claim 1, wherein the temperature is +10° C. to +70° C.

8. A process according to claim 1, wherein the temperature is +20° C. to +60° C.

9. A process according to claim 1, wherein the pressure is 1 to 15 bar.

10. A process according to claim 1, wherein the pressure is 1 to 10 bar.

11. A process according to claim 1, which further comprises adding a phase transfer catalyst during the isomerization.

12. A process according to claim 11, wherein the phase transfer catalyst is tetraethylammonium chloride.

13. A process according to claim 11, wherein the phase transfer catalyst is added in amounts of 0.1 to 10 mole % relative to the isopropyl chloride.

14. A process according to claim 11, wherein the phase transfer catalyst is added in amounts of 1 to 4 mole % relative to the isopropyl chloride.

15. A process according to claim 1, which further comprises adding 1,2-propanediol during the isomerization.

16. A process according to claim 15, wherein the 1,2-propanediol is added in amounts of 0.1 to 10 mole % relative to the isopropyl chloride.

17. A process according to claim 15, wherein the 1-2-propanediol is added in amounts of 2 to 5 mole % relative to the isopropyl chloride.

* * * * *